United States Patent [19]

Shawl et al.

[11] Patent Number: 4,978,779

[45] Date of Patent: * Dec. 18, 1990

[54] PREPARATION OF METHYLENE DIPHENYLENE DIISOCYANATES AND POLYMETHYLENE POLYPHENYLENE POLY (ISOCYANATES) USING AN ORGANIC SULFONIC ACID PROMOTER

[75] Inventors: Edward T. Shawl, Wallingford; Haven S. Kesling, Jr., Drexel Hill; Frank J. Liotta, Jr., Collegeville, all of Pa.

[73] Assignee: Arco Chemical Technology, Inc., Wilmington, Del.

[*] Notice: The portion of the term of this patent subsequent to Nov. 28, 2006 has been disclaimed.

[21] Appl. No.: 321,496

[22] Filed: Mar. 9, 1989

[51] Int. Cl.$^5$ .............................. C07C 69/00
[52] U.S. Cl. .................................... 560/344
[58] Field of Search ........................... 560/344

[56] References Cited

U.S. PATENT DOCUMENTS

| | | |
|---|---|---|
| 2,773,086 | 12/1966 | Slocombe et al. |
| 3,898,259 | 8/1975 | Hearsey ............................ 560/344 |
| 3,936,484 | 2/1976 | Rosenthal et al. ............... 560/344 |
| 4,153,624 | 5/1979 | Fern et al. ......................... 560/344 |
| 4,223,145 | 9/1980 | Hentschel ......................... 560/344 |
| 4,596,679 | 6/1986 | Hellbach .......................... 560/344 |
| 4,883,908 | 11/1989 | Shawl et al. ...................... 560/344 |

OTHER PUBLICATIONS

Hofmann, Proc. Royal Soc. London 9,274 (1858).
Hofmann, Chem. Ber. 3, 653 (1870).
Iwakura et al Bull. Tokyo Inst. Tech. 13, 25(195); Chem. abs. 44, 3924e (1950).
Bennet et al, J. Am. Chem, Soc. 75, 210(1952).

*Primary Examiner*—Alan Siegel
*Attorney, Agent, or Firm*—Delbert E. McCaslin

[57] ABSTRACT

An improved process is provided for the preparation of methylene diphenylene diisocyanates (MDI) and polymethylene polyphenylene poly (isocyanates) (PMDI) by the thermal decomposition of a methylene diphenylene bis (dialkylurea) or a polymethylene polyphenylene poly (alkylurea) in a solvent in the presence of an organic sulfonic acid or sulfonated aromatic ion exchange resin as a promoter for conversion of the urea groups to the corresponding isocyanate.

18 Claims, No Drawings

PREPARATION OF METHYLENE DIPHENYLENE DIISOCYANATES AND POLYMETHYLENE POLYPHENYLENE POLY (ISOCYANATES) USING AN ORGANIC SULFONIC ACID PROMOTER

FIELD OF THE INVENTION

The present invention relates to an improved process for the preparation of methylene diphenylene diisocyanates and the higher polymethylene polyphenylene poly (isocyanates) homologs thereof (commonly known in the trade as MDI and PMDI respectively) by heating in an inert solvent a methylene diphenylene bis (dialkylurea) or a polymethylene polyphenylene poly (alkylurea) in the presence of an organic sulfonic acid as a promoter to convert the urea groups to isocyanate groups and recovering the methylene diphenylene diisocyanates or poly methylene polyphenylene poly (isocyanates) from the reaction mixtures.

BACKGROUND OF THE INVENTION

A number of processes have been reported for the preparation of various diisocyanates and polyisocyanates by the vapor or solvent phase decomposition of substituted ureas.

The production of aromatic isocyanates from symmetrical bis aryl ureas in a solventless system in the presence of hydrogen chloride, phosphorus pentoxide or zinc chloride was described by A. Hofmann in the Proc. Royal Soc., London, Vol. IX, p. 274 (1858). By heating a mixture of diphenyl urea with phosphorus pentoxide, zinc chloride or gaseous HC1, Hofman distilled phenyl isocyanate overhead. No details of the experimental procedure are presented and the yield of isocyanate is not given.

A. Hofmann, Chemisch Berichte, Vol. 3, pp. 653-658 (1870) described heating diphenyl urea in the presence of phosphorus pentoxide giving yields too small to be considered for the preparation of the isocyanate.

Subsequent work by Iwakura and Nagakubo reported in the Bulletin Tokyo Inst. Technol., Vol. 13, p. 25 (1950) and Chemical Abstracts, Vol. 44, p. 3924e (1950) describes the preparation of an aromatic isocyanate (p-ethoxyphenylisocyanate) by heating a solution of bis aryl urea such as bis (p-ethoxyphenyl) urea in the presence of hydrogen chloride gas.

The vapor phase decomposition of bis aryl ureas at 350° C. and higher temperatures has been described by W. D. Bennet et al, Journ. Am. Chem. Soc., Vol. 75, p. 2101 (1952) and Slocombe et al in U.S. Pat. No. 2,773,086, Dec. 4, 1956 in the presence of gaseous HCl as a promoter. Yields are reported in the 60 to 70% range for the vapor phase reaction and only a 5% yield for liquid phase reaction. A carbamoyl chloride intermediate is formed.

The liquid phase decomposition of trisubstituted ureas to isocyanates has been described by van Landeghem et al, French Pat. No. 1,473,821, Feb. 13, 1967; C. J. Hearsey, U.S. Pat. No. 3,898,259, Aug. 5, 1975 and Rosenthal et al in U.S. Pat. No. 3,936,484, Feb. 3, 1976. Van Landeghem shows thermal decomposition of trisubstituted ureas in an organic solvent having specified dielectric constants at 140° to 170° C. with long reaction times of from 6 to 10 hours and modest yields of 60 to 75%. A variety of catalysts are shown but not exemplified or claimed, and include metal salts, such as acetates, stearates, and linoleates of manganese, zinc, cobalt, chromium and vanadium, tertiary amine bases, such as aliphatic, cycloaliphatic, aromatic and mixed tertiary amines, aliphatic heterocyclic amines such as N-methylpiperidine or N, N'-dimethylpiperidine as well as aromatic heterocyclic amines such as pyridine and pyrimidine. Other nitrogen compounds such as imidazole are indicated as being suitable. However, under the reaction conditions described tertiary amines as shown by van Landeghem do not catalyze urea decomposition.

Rosenthal et al U.S. Pat. No. 3,936,484 discloses the thermal decomposition of di- and tri-substituted ureas to isocyanates at temperatures above 230° C. in a solvent and isocyanate yields of from 60 to 80%.

The Hearsey U.S. Pat. No. 3,898,259 describes the introduction of gaseous hydrogen chloride into the liquid phase urea decomposition reaction to give reduced reaction times with isocyanate yields of from 80-90%. An excess of gaseous HCl is employed and a by-product carbamoyl chloride intermediate is formed.

A. Hentschel et al U.S. Pat. No. 4,223,145, Sep. 16, 1980 discloses the formation of an HCl adduct of a trisub-substituted urea using at most a 10% excess of HCl. This adduct is then decomposed in a closed system at from 80°-180° C.

Applicants have found that organic sulfonic acids are very effective promoters for the thermal decomposition of methylene diphenylene bis (dialkylureas) and polymethylene polyphenylene poly (alkylureas) to the corresponding isocyanate at relatively mild reaction temperatures and short residence times in an organic solvent.

SUMMARY OF THE INVENTION

This invention relates to a novel improved process for the preparation of methylene diphenylene diisocyanates (MDI) and polymethylene polyphenylene poly (isocyanates) (PDMI) from methylene diphenylene bis (dialkylurea) or polymethylene polyphenylene poly (alkylurea) which comprises thermally treating the respective urea which has been dissolved in or slurried with an inert organic solvent in the presence of an organic sulfonic acid to produce the corresponding isocyanate. The MDI or PMDI produced by the instant invention are of significant industrial importance and are particularly useful as intermediates in producing products for agricultural application and in the preparation of polyurethanes.

It is an object of the present invention therefore, to provide an improved process for the production of MDI and PMDI from the corresponding urea in high yield and high conversion of the urea.

It is another object of this invention to provide an improved reaction (thermal decomposition) system for the conversion of the bis (dialkyl ureas) and the poly (alkyl ureas) to the corresponding isocyanates.

These and other objects and advantages of this invention will become apparent from the description of the invention which follows and the claims.

DETAILED DESCRIPTION OF THE INVENTION

In accordance with the present invention, methylene diphenylene diisocyanates or polymethylene polyphenylene poly (isocyanates) are produced by heating at temperatures of from about 50° C. to about 220° C. preferably from about 90° C. to 150° C., a methylene diphenylene bis (dialkylurea) having the general formula

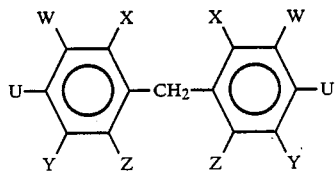

or the higher polymethylene polyphenylene poly (alkylurea) homologs thereof having the structural formula

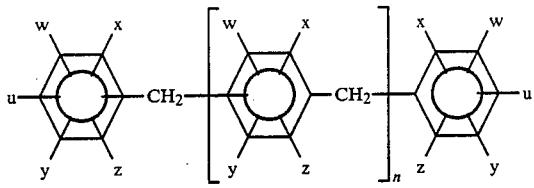

wherein at least one of the substituents u, w, x, y and z on the ring is a dialkylureido (—NHCONRR′) group and the other substituents which may be different on the ring, are hydrogen, an ether group or a nitro group, R and R′ which may be the same or different are an alkyl group having independently from 1 to 8 carbon atoms and n is an integer of from 1 to 8 dissolved or slurried in an organic solvent or mixture of solvents, which are stable and substantially chemically inert to the components of the reaction system, in the presence of an organic sulfonic acid promoter such as an alkane sulfonic, halogenated alkane sulfonic acid and aromatic sulfonic resins or acidic sulfonated aromatic ion exchange resins or perfluoroalkane sulfonic acid resins to convert the urea groups to isocyanate groups and the desired methylene diphenylene diisocyanate or polymethylene polyphenyl poly (isocyanate) product separated and recovered.

The R′ and R″ of the dialkylureido (—NHCONRR′) group set forth hereinabove may be substituted or unsubstituted mono-, di-or trivalent radicals selected from saturated or mono-olefinic unsaturated straight or branched chain aliphatic or cycloaliphatic radicals optionally containing alkoxyalkyl radicals with one or more ether linkages, aryl radicals, or aralkyl radicals. These radicals may be substituted with groups which are non-reactive with the isocyanates produced by the process of the invention, such as, for example, nitro or halo groups. Also included are cycloaliphatic and substituted cycloaliphatic radicals containing from 5 to 7 carbon atoms such as cyclopentyl, cyclohexyl and cycloheptyl radicals.

Representative methylene diphenylene bis (dialkylureas) which may be employed in the process of the present invention) include, for example, methylene diphenylene bis (dimethylurea), methylene diphenylene bis (diethylurea), methylene diphenylene bis (dibutylurea) and the like as well as the polymethylene polyphenylene poly (methylurea), polymethylene polyphenylene poly (ethyl or butyl or propyl ureas) and the like. These urea compounds are merely representative of a large number of ureas falling within the above described formulae which can be converted to the corresponding isocyanates in the solvent phase in the presence of an organic sulfonic acid as a promoter.

Aromatic dialkyl ureas and processes for their preparation have been described in the literature. Bis (dialkylureas) of toluene and other similar ureas may be prepared, for example, by reacting toluene-2,4-diisocyanate with diethylamine as is described in Japanese Kokai No. 76/149,400.

The organic sulfonic acids employed in the process of the present invention to promote the thermal decomposition of the aromatic methylene diphenylene bis (dialkylurea) or the higher polymethylene polyphenylene poly (alkylureas) to the corresponding isocyanates may be an alkane sulfonic acid or a halogenated alkane sulfonic acid having up to 10 carbon atoms in the alkyl group, or an aromatic sulfonic acid which may contain substituents on the aromatic ring such as halogens, alkyl radicals, aromatic radicals, nitro groups and the like. The organic sulfonic acid may be in the form of an acidic sulfonated aromatic ion exchange resin such as, for example, the sulfonated styrene/divinylbenzene copolymer (sold, for example, commercially as "Amberlyst 15" by Rohm and Haas Co.) and having a bulk density of approximately 4.9 milliequivalents/g. dry, a surface area of from about 40 to 50 $M^2/g$. and an average pore diameter of from about 200 to 600 Angstrom units, or an acidic perfluoroalkane sulfonic acid resin such as "Nafion" (sold for example, commercially by the DuPont Co.) and having an equivalent weight of between about 110 and 1500, a hydrogen ion concentration of between about 0.7–1.0 milliequivalents/g. dry and prepared, for example, by the polymerization of tetrafluoroethylene with a sulfonyl fluoride vinyl ether, followed by saponification with caustic to form the metal salt and treatment with an acid to convert the salt to the sulfonic acid form. Mixtures of the sulfonic acid promoters may be employed but it is preferable to use a single acid promoter to simplify separation and recovery of the aromatic isocyanate produced. Representative organic sulfonic acid promoters suitable for use in the process of this invention include, for example, methane, ethane, butane, hexane sulfonic acids, and the like, trifluoromethane sulfonic acid, benzene sulfonic acid, 1,3-benzene disulfonic acid, p-toluene sulfonic acid, naphthalene sulfonic acid, 4-chloro-3-nitrobenzene sulfonic acid, 3 nitrobenzene sulfonic acid, and the like, as well as the sulfonated aromatic ion exchange resins which include the "Amberlyst 15" and "Nafion" described hereinabove and also include the "Dowex 50" (Dow Chemical), "AG50W" (Bio-Rad), and "Amberlite" (Rohm and Haas) resin materials. The ion exchange resins may be supplied commercially in the hydrogen ion form or the salt form such as the sodium or potassium salt. The salt can readily be converted to the active hydrogen ion form by, for example, treating with aqueous hydrochloric acid, washing with water to a constant pH in the range of 5.5 to 7 and then drying to remove residual water.

The organic sulfonic acid promoter is generally employed in the process of the instant invention at a molar ratio of one to one based on the urea groups to sulfonic acid groups. No advantage is gained by using large excess amounts which may lead to by-product formation.

The process of the present invention can be suitably carried out by adding the bis (dialkyl urea) or poly (alkyl ureas) to a solvent or a mixture of solvents comprising the reaction medium. The urea may be soluble in the solvent or solvents or soluble at reaction temperatures or the urea may be in the form of a slurry. Suitable solvents which may be employed include, for example, the aromatic hydrocarbons such as benzene, toluene, xylene, trimethylbenzene, tetrahydronapthalene as well as the higher alkyl-substituted aromatic hydrocarbons alkanes and substituted alkanes as well as cycloalkanes having from 5 to 20 carbon atoms such as, for example, n-hexane, n-heptane, octane, nonane, cyclohexane, dodecane, octadecane, 2-methylhexane, 2-ethylhexane, methylcyclohexane, and the like; halogenated or nitrated aromatic and aliphatic hydrocarbons such as, for example, methylene chloride, carbon tetrachloride, 1,2-dichloroethane, tetrachloroethane chlorobenzenes, nitrobenzenes, dinitrotoluene and the like; aromatic or aliphatic ethers such as, for example diphenylether; dibutylether, propyleneglycol dimethyl ether, and the like; tertiary amines, such as, for example, pyridine, triethylamine, N-methylpyrrolidone and the like.

The process of the present invention may be carried out as a batch, semi-continuous or continuous process and the order of addition of the materials and reactants may be varied to suit the particular apparatus and sulfonic acid employed. For example, in a batch process all the dialkylurea or poly (alkyl urea), the solvent and the organic sulfonic acid may be charged together to the reaction vessel and then heated to the desired reaction temperature, or, the particular urea and solvent may be added to the reactor as solution or slurry and heated to the desired reaction temperature, and then the sulfonic acid promoter added alone or in additional solvent. The sulfonic acid promoter may also be added to the reactor, heated to the desired temperature and then the urea in solvent added. The added materials can be maintained at any convenient temperature.

The reaction of the invention may be carried out in any suitable reactor which is equipped with a means for temperature control and agitation. Heating and/or cooling means may be employed interior or exterior of the reaction vessel to maintain temperature within the desired range.

As indicated hereinabove, the thermal decomposition of the bis (dialkyl ureas) or poly (alkyl ureas) is carried out at temperature of from about 50° C. to about 220° C., preferably from about 90° C. to 150° C. Reaction time is dependent on decomposition temperature but will generally range between about 5 minutes and several hours. The reaction is generally carried out at atmospheric pressure, but depending on the boiling points of the solvents employed and the isocyanate product produced, it may be carried out at super-atmospheric or sub-atmospheric pressures. The isocyanates formed may be recovered by filtration, by distillation, or by other known methods, and will depend on the solvent and the isocyanate produced.

The present invention is more fully illustrated by the following examples, which include particular features of the invention. However, the examples are not to be construed as limiting the invention in any way, it being understood that numerous variations are possible without departing from the spirit and scope of the invention.

EXAMPLE 1

A mixture of 2.0 g polymethylene polyphenylene poly (diethylurea), 1.26 g methanesulfonic acid and 106 g toluene was added to a 500 ml, 3-neck, fluted, round bottom flask equipped with a bottom take-off, mechanical stirrer, condenser and a thermocouple for measuring reaction temperature. The mixture was heated to a 110° C. for 15 min with vigorous agitation. Analysis of the toluene phase by infrared spectroscopy showed an 81% yield of polymethylene polyphenylene polyisocyanate.

EXAMPLE 2

A mixture of 3.95 g 4,4'-methylene diphenylene bis (diethylurea) in 200 g o-xylene was charged to the apparatus used in Example 1. The mixture was heated to reflux at 144° C. and then 2.1 g, 22 mmoles of methanesulfonic acid was added in one portion. The mixture was stirred for 30 min at reflux and then the phases were allowed to settle at 50° C. The bottom salt phase was drawn off through the bottom take-off. Analysis of the xylene phase by high pressure liquid chromatography (HPLC) and infrared (IR) analysis showed 100% conversion of the 4,4'-methylene diphenylene diisocyanate (MDI). Xylene was removed by distillaton in a rotary evaporator to give 1.6 g of crude MDI corresponding to a 90% isolated yield.

EXAMPLES 3 to 8

The following runs were made using the procedures of Example 1. Products were analyzed by a combination of infrared and HPLC analysis. Reaction materials, conditions and analytical results are set forth in the following Table.

TABLE

| | | EXAMPLES 3–8 | | | | |
|---|---|---|---|---|---|---|
| Ex. No. | Urea (g)* | Acid (g) | Solvent (g) | Temp. (°C.) | Time (Min) | % Yield NCO |
| 3 | MUMDI (3.4) | p-Toluene-SO$_3$H (4) | Chlorobenzene (150) | 130 | 45 | 82 |
| 4 | MUMDI (6.8) | CH$_3$SO$_3$H (4) | Mixed Xylenes (100) | 140 | 30 | 97 |
| 5 | EUPMDI 2.0 | Benzene SO$_3$H (2.0) | Diphenylether (100) | 180 | 15 | 80 |
| 6 | EUMDI (3.9) | CF$_3$SO$_3$H (3.1) | Tetrachlorethane (150) | 90 | 30 | 92 |
| 7 | MUPMDI (10.0) | CH$_3$SO$_3$H (6.0) | Mesitylene (100) | 160 | 20 | 95 |
| 8 | BUMDI (5.1) | C$_2$H$_5$SO$_3$H (2.7) | Toluene (100) | 110 | 60 | 88 |

*MUMDI = Methylene diphenylene bis (dimethylurea)
EUMDI = Methylene diphenylene bis (diethylurea)
BUMDI = Methylene diphenylene bis (dibutylurea)
MUPMDI = Polymethylene polyphenylene poly (dimethylurea)
EUPMDI = Polymethylene polyphenylene poly (diethylurea)

EXAMPLE 9

A 250 g sample of "DOWEX" 50X2-400 ion exchange resin was washed with three 350 ml portions of hydrochloric acid to convert the resin to the hydrogen ion form. The resin was then washed with three 350 ml portions of distilled water and dried in a vacuum oven at 75° C. Ten grams of the dried resin was combined with 5.0 g of 4,4'-methylene diphenylene bis (diethylurea) and 60 ml o-xylene in a round bottom flask. The mixture was heated at 144° C. for 4 hours under a nitrogen atmosphere. Throughout the reaction a slow nitrogen purge was maintained through the solution. At the end of the reaction time, the mixture was cooled to room temperature and the solid resin was removed by filtration. Analysis of the xylene solution by HPLC after addition of ethanol to convert the MDI to its ethyl carbamate derivative shows an 82% yield of methylene diphenylene diisocyanate.

EXAMPLE 10

The procedure of Example 9 was repeated using 5.0 g of polymethylene polyphenylene poly bis (dimethylurea) with 60 ml, 1,2 - dichlorobenzene and 10 g "Amberlyst 15" resin. The mixture was heated for 2 hours at 180° C. Analysis of the product by infrared analysis showed an 85% yield of the respective PMDI.

We claim:

1. A process for the preparation of a methylene diphenylene diisocyanate or a polymethylene polyphenylene poly (isocyanate) which comprises heating at a temperature within the range of from about 50° C. to about 220° C. a methylene diphenylene bis (dialkylurea) having the formula

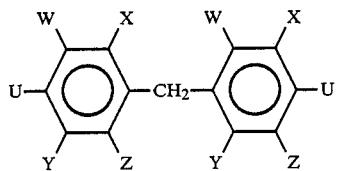

or a polymethylene polyphenylene poly (alkylurea) having the formula

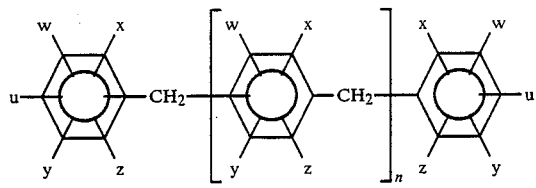

wherein at least one of the substituents u, w, x, y and z on the ring is a dialkylureido (—NHCONRR') group and the other substituents which may be the same or different on the ring, are hydrogen, an ether group or a nitro group, R and R' of the dialkylureido group which may be the same or different are an alkyl group having independently from 1 to 8 carbon atoms and n is an integer of from 1 to 8, dissolved or slurried in an organic solvent or mixture of solvents, in the presence of an organic sulfonic acid or sulfonated aromatic ion exchange resin as a promoter to convert the urea to the corresponding isocyanate, and thereafter separating and recovering the diisocyanate or poly (isocyanate).

2. A process according to claim 1 wherein the temperature is in the range of from 90° C. to 150° C.

3. A process according to claim 1 wherein the methylene diphenylene bis (dialkylurea) is selected from the group consisting of methylene diphenylene bis (dimethylurea), methylene diphenylene bis (diethylurea) and methylene diphenyl bis (di-n-butylurea).

4. A process according to claim 3 wherein the methylene diphenylene bis (dialkyl urea) is methylene diphenylene bis (diethylurea).

5. A process according to claim 1 wherein the polymethylene polyphenylene poly (alkylurea) is polymethylene polyphenylene poly (dimethylurea).

6. A process according claim 1 wherein the organic solvent is selected from the group consisting of toluene, o-xylene, mesitylene, diphenylether, chlorobenzene and tetrachloroethane.

7. A process according of claim 6 wherein the solvent is toluene.

8. A process according to claim 6 wherein the solvent is o-xylene.

9. A process according to claim 1 wherein the organic sulfonic acid is selected from the group consisting of methane sulfonic acid, ethane sulfonic acid, butane sulfonic acid, p-toluene sulfonic acid, trifluoromethane sulfonic acid and benzene sulfonic acid.

10. A process according to claim 9 wherein the organic sulfonic acid is methane sulfonic acid.

11. A process according to claim 1 wherein the sulfonated aromatic ion exchange resin is selected from the group consisting of sulfonated styrene/divinylbenzene copolymer resins and acidic perfluoralkane sulfonic acid resins.

12. A process for the preparation of a methylene diphenylene diisocyanate which comprises heating at a temperature of from about 90° C. to about 150° C. a methylene diphenyl bis (dialkylurea) having the formula

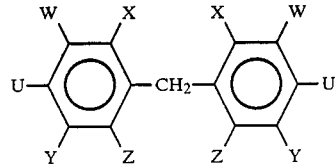

wherein at least one of the substituents u, w, x, y and z on the ring is a dialkylureido (—NHCONRR') group and the other substituents on the ring which may be the same or different are hydrogen, an ether group or a nitro group and R and R' of the dialkylureido group are an alkyl group having independently from 1 to 8 carbon atoms, dissolved in or slurried in an organic solvent or mixture of solvents in the presence of an organic sulfonic acid or sulfonated aromatic ion exchange resin as a promoter to convert the urea to the isocyanate and thereafter separating and recovering the isocyanate.

13. A process according to claim 12 wherein the methylene diphenylene bis (dialkylurea) is methylene diphenylene bis (diethylurea).

14. A process according to claim 12 wherein the organic solvent is o-xylene.

15. A process according to claim 12 wherein the sulfonated aromatic ion exchange resin is a sulfonated styrene/divinylbenzene copolymer resin.

16. A process according to claim 12 wherein the sulfonated aromatic ion exchange resin is a perfluoroalkane sulfonic acid resin.

17. A process according to claim 1 wherein the molar ratio of dialkylureido groups to sulfonic acid groups is 1:1.

18. A process according to claim 12 wherein the molar ratio of dialkylureido groups to sulfonic acid groups is 1:1.

* * * * *